(12) United States Patent
Desai et al.

(10) Patent No.: US 9,845,303 B2
(45) Date of Patent: Dec. 19, 2017

(54) PROCESS FOR THE PREPARATION OF DAPAGLIFLOZIN

(71) Applicant: CADILA HEALTHCARE LIMITED, Ahmedabad, Gujarat (IN)

(72) Inventors: Sanjay Jagdish Desai, Ahmedabad-Gujarat (IN); Jayprakash Ajitsingh Parihar, Ahmedabad-Gujarat (IN); Mahesh Laljibhai Rupapara, Ahmedabad-Gujarat (IN)

(73) Assignee: Cadila Healthcare Limited, Ahmedabad (IN)

( * ) Notice: Subject to any disclaimer, the term of this patent is extended or adjusted under 35 U.S.C. 154(b) by 17 days.

(21) Appl. No.: 15/297,406

(22) Filed: Oct. 19, 2016

(65) Prior Publication Data
US 2017/0166547 A1    Jun. 15, 2017

(30) Foreign Application Priority Data

Oct. 19, 2015  (IN) .......................... 3959/MUM/2015
Nov. 9, 2015   (IN) .......................... 4285/MUM/2015
Nov. 30, 2015  (IN) .......................... 4496/MUM/2015
Apr. 20, 2016  (IN) ............................. 201621013770

(51) Int. Cl.
    *C07D 309/10*    (2006.01)
(52) U.S. Cl.
    CPC ........ *C07D 309/10* (2013.01); *C07B 2200/13* (2013.01)

(58) Field of Classification Search
    CPC .................................................. C07D 309/10
    See application file for complete search history.

(56) References Cited

U.S. PATENT DOCUMENTS

| | | |
|---|---|---|
| 6,515,117 B2 | 2/2003 | Ellsworth et al. |
| 7,919,598 B2 | 4/2011 | Gougoutas et al. |
| 8,999,941 B2 | 4/2015 | Henschke et al. |
| 2013/0303467 A1 | 11/2013 | Gougoutas et al. |

FOREIGN PATENT DOCUMENTS

| | | |
|---|---|---|
| WO | 2013/079501 A1 | 6/2013 |
| WO | 2015/011113 A1 | 1/2015 |
| WO | 2015/104658 A2 | 7/2015 |
| WO | 2015/117538 A1 | 8/2015 |
| WO | 2015/128853 A1 | 9/2015 |
| WO | 2015/132803 A2 | 9/2015 |

OTHER PUBLICATIONS

Espacenet English abstract of WO 2015/117538 A1.

*Primary Examiner* — Noble Jarrell
*Assistant Examiner* — John S Kenyon
(74) *Attorney, Agent, or Firm* — Ladas & Parry LLP (57) ABSTRACT

Dapagliflozin compounds and process for dapagliflozin preparation are described. Pharmaceutical compositions comprising dapagliflozin or solvates of dapagliflozin, for the treatment of diabetes are also described.

15 Claims, 7 Drawing Sheets

PROCESS FOR THE PREPARATION OF DAPAGLIFLOZIN

FIELD OF THE INVENTION

The field of the present invention relates to processes for the preparation of dapagliflozin. In particular, the present invention relates to a stable amorphous dapagliflozin and process for its preparation. The present invention also relates to pharmaceutical compositions comprising the stable amorphous form or solvates of dapagliflozin, for the treatment of diabetes.

BACKGROUND OF THE INVENTION

The following discussion of the prior art is intended to present the invention in an appropriate technical context and allow its significance to be properly appreciated. Unless clearly indicated to the contrary, however, reference to any prior art in this specification should be construed as an admission that such art is widely known or forms part of common general knowledge in the field.

FARXIGA® is a sodium-glucose cotransporter 2 (SGLT2) inhibitor indicated as an adjunct to diet and exercise to improve glycemic control in adults with type 2 diabetes mellitus. The active ingredient of the approved product FARXIGA Dapagliflozin, which is described chemically as D-glucitol, 1,5-anhydro-1-C-[4-chloro-3-[(4-ethoxyphenyl)methyl]phenyl]-,(1S)-, compounded with (2S)-1,2-propanediol, hydrate (1:1:1). The empirical formula is $C_{21}H_{25}ClO_6 \cdot C_3H_8O_2 \cdot H_2O$ and the molecular weight is 502.98. The structural formula is:

U.S. Pat. No. 6,515,117 discloses the compound dapagliflozin and a process for its preparation wherein dapagliflozin is obtained as glassy off-white solid having 94% purity and containing 0.11 mol % of EtOAc.

U.S. Pat. No. 7,919,598, U.S. PG-Pub. No. 2013/0303467 and International (PCT) Publication No. WO 2013/079501 discloses various crystalline forms of dapagliflozin viz. hydrates, anhydrous forms, solvates and complexes with amines and amino acids.

U.S. Pat. No. 8,999,941 discloses a process for preparation of amorphous dapagliflozin comprising adding a heated solution of dapagliflozin in toluene into n-heptane. After drying in vacuo the product was obtained as a white solid with melting point of 49.5° C. to 62.6° C. DSC analysis showed the existence of two endothermic transitions at 57° C. and 107° C. which were indicative of dehydration and solvent evaporation. The prior art fails to describe the purity and level of the residual solvents in final product.

International (PCT) Publication No. WO 2015/011113 discloses an amorphous solid dispersion of dapagliflozin and a polymer as well as process for its preparation.

International (PCT) Publication No. WO 2015/104658 discloses a process for the preparation of an amorphous form of dapagliflozin by dissolving dapagliflozin in solvents and removing the solvent. Also disclosed is an amorphous solid dispersion of dapagliflozin together with one or more pharmaceutically acceptable carriers as well as process for its preparation.

International (PCT) Publication No. WO 2015/128853 discloses a pharmaceutical composition comprising a solid dispersion of dapagliflozin and one or more pharmaceutically acceptable excipients and process for the preparation thereof.

International (PCT) Publication No. WO 2015/132803 discloses crystalline glycerol solvate of dapagliflozin and process for its preparation by treating dapagliflozin with glycerol in water.

International (PCT) Publication No. WO 2015/117538 discloses new dapagliflozin crystalline form with absorption peak at about 4.318(20.45) in X-ray powder diffraction pattern shown by angle 2θ and inter planar spacing (value d) and process for its preparation.

Solvates and hydrates can be very stable solid forms and may have definite benefits in regard to manufacturing. Stable polymorphic forms of dapagliflozin can be crystallized as solvates of the present invention.

Crystalline solids normally require a significant amount of energy for dissolution due to their highly organized, lattice like structures. For example, the energy required for a drug molecule to escape from a crystal is more than from an amorphous or a non-crystalline form. It is known that the amorphous forms in a number of drugs exhibit different dissolution characteristics and in some cases different bioavailability patterns compared to the crystalline form (Econno T., *Chem. Pharm. Bull.*, 1990; 38: 2003-2007). For some therapeutic indications, one bioavailability pattern may be favoured over another.

An amorphous form of some of the drugs exhibit much higher bioavailability than the crystalline forms, which leads to the selection of the amorphous form as the final drug substance for pharmaceutical dosage from development. Additionally, the aqueous solubility of crystalline form is lower than its amorphous form in some of the drugs, which may have resulted in the difference in their in-vivo bioavailability. Therefore, it is desirable to have amorphous forms of drugs with high purity to meet the needs of regulatory agencies and also highly reproducible processes for their preparation.

As discussed herein above, the current art processes provides an amorphous dapagliflozin with low purity and high residual solvents which is not suitable for pharmaceutical preparations. Therefore, there still exists a need to provide an efficient process for preparation of an amorphous dapagliflozin that provides dapagliflozin with higher purity and lower levels of residual solvent(s) in accordance with the ICH guidelines which is suitable for pharmaceutical preparations.

SUMMARY OF THE INVENTION

In one general aspect, there is provided a stable amorphous dapagliflozin.

In another general aspect, there is provided a process for the preparation of amorphous dapagliflozin.

In another aspect, there is provided a process for the preparation of amorphous dapagliflozin, the process comprising:
(a) treating dapagliflozin or its solvates with water;
(b) stirring the reaction mixture at 80° C. to 90° C.;
(c) adding isopropyl alcohol at 70° C. to 75° C.;

(d) stirring the reaction mixture at 5° C. to 10° C. for 16-18 hours;
(e) filtering the product;
(f) drying the product under vacuum for 20 to 24 hours below 25° C.;
(g) drying the product under vacuum for 20 to 24 hours at 25° C. to 30° C.;
(h) drying the product under vacuum for 18 to 20 hours at 35° C. to 40° C. till water content is less than 3.0%; and
(i) optionally drying the product under vacuum for 18 to 21 hours at 40° C. to 45° C. to obtain the amorphous dapagliflozin.

In another general aspect, there are provided dapagliflozin solvates of Formula (III) with one or more solvents, Formula (III)

wherein X is 1,2-butanediol, 1,2-pentanediol, 1,2-hexanediol, 1,2-heptanediol (S)-1,2-butanediol, (R)-1,2-butanediol, (S)-1,2-pentanediol, (R)-1,2-pentanediol, (S)-1,2-hexanediol, (R)-1,2-hexanediol, (S)-1,2-heptanediol or (R)-1,2-heptanediol or mixture or hydrates thereof, which may be monohydrate, dihydrates or higher hydrates.

The dapagliflozin solvates of Formula (III) with one or more solvents may be in crystalline form.

In another aspect, there is provided a process for the preparation of dapagliflozin solvates of Formula (III), Formula (III)

wherein X is 1,2-butanediol, 1,2-pentanediol, 1,2-hexanediol, 1,2-heptanediol, (S)-1,2-butanediol, (R)-1,2-butanediol, (S)-1,2-pentanediol, (R)-1,2-pentanediol, (S)-1,2-hexanediol, (R)-1,2-hexanediol, (S)-1,2-heptanediol or (R)-1,2-heptanediol or mixture or hydrates thereof, which may be monohydrate, dihydrates or higher hydrates, the process comprising:
(a) preparing a solution of dapagliflozin in one or more solvents;
(b) adding a diol and one or more second solvents to obtain a reaction mixture;
(c) stirring the reaction mixture at 0-5° C.; and
(d) obtaining the dapagliflozin solvate.

In another general aspect, there is provided a crystalline Form Z of dapagliflozin.

In another aspect, there is provided a process for the preparation of crystalline Form Z of dapagliflozin, the process comprising:

(a) preparing a suspension of dapagliflozin solvate in water;
(b) heating the suspension to obtain a solution;
(c) adding one or more solvents to the solution to obtain a reaction mixture;
(d) cooling the reaction mixture, and
(e) obtaining the crystalline Form Z of dapagliflozin.

The crystalline Form Z of dapagliflozin may be characterized by X-ray powder diffraction pattern. The X-ray powder diffraction pattern may be substantially the same as that shown in FIG. 1.

In another general aspect, there is provided a pharmaceutical composition comprising crystalline Form Z of dapagliflozin and one or more pharmaceutically acceptable excipients, diluents and carriers.

In another general aspect, there is provided a stable amorphous dapagliflozin having a purity of about 99% or more, when measured by area percentage of HPLC.

In another general aspect, there is provided a pharmaceutical composition comprising a stable amorphous dapagliflozin having one or more pharmaceutically acceptable carriers, excipients or diluents.

DETAILED DESCRIPTION OF THE INVENTION

The above and other objects of the present invention are achieved by the process of the present invention, which leads to a stable amorphous dapagliflozin suitable for pharmaceutical preparations and having greater stability. The invention also provides a process for preparing a stable amorphous dapagliflozin.

All ranges recited herein include the endpoints and the terms "about", "from", "to" are to be construed as modifying a value they are applied to such that it is not absolute and includes, to the very least, the degree of expected experimental error, limitation of method or instrument error for a given technique used to measure the value.

As used herein, the term "solution" or "reaction mixture" does not limit to a clear solution only and includes any hazy or opaque mass obtained.

As used herein, the term "stable amorphous dapagliflozin" includes amorphous dapagliflozin that does not convert to any other solid form when stored at a temperature of up to about 40° C. and at a relative humidity of about 25% to about 75% for about three months or more.

As used herein, the terms "obtaining" means isolating the amorphous form of dapagliflozin by way of filtration, filtration under vacuum, centrifugation, decantation. The product obtained may be further or additionally dried to achieve the desired moisture values. For example, the product may be dried in a tray drier, dried under vacuum and/or in a Fluid Bed Drier.

The term "composition" used herein means a physical mixture of two or more components.

As used herein, "Particle Size Distribution (PSD)" means the cumulative volume size distribution of equivalent spherical diameters as determined by laser diffraction in Malvern Master Sizer 2000 equipment or its equivalent.

The important characteristics of the PSD are the (D90), which is the size, in microns, below which 90% of the particles by volume are found, and the (D50), which is the size, in microns, below which 50% of the particles by volume are found. Thus, a D90 or d(0.9) of less than 450 microns means that 90 volume-percent of the particles in a composition have a diameter less than 450 microns.

The term "pharmaceutically acceptable" means that which is useful in preparing a pharmaceutical composition that is generally non-toxic and is not biologically undesirable, and includes that which is acceptable for veterinary use and/or human pharmaceutical use.

The term "pharmaceutical composition" is intended to encompass a drug product including the active ingredient(s), pharmaceutically acceptable excipients that make up the carrier, as well as any product which results, directly or indirectly, from combination, complexation or aggregation of any two or more of the ingredients. Accordingly, the pharmaceutical compositions encompass any composition made by admixing the active ingredient, active ingredient dispersion or composite, additional active ingredient(s), and pharmaceutically acceptable excipients.

In one general aspect, there is provided a stable amorphous form of dapagliflozin.

In another general aspect, there is provided an amorphous form of dapagliflozin having purity by HPLC greater than 99% and residual solvents less than 0.5%.

In general, the amorphous form of dapagliflozin is substantially free from residual solvents. The term "substantially free" means residual solvents within the permissible ICH limits suitable for pharmaceutical preparations. For example but not limited to less than 0.5%, particularly less than 0.3% or more particularly less than 0.2%.

In one general aspect there is provided a compound of general Formula (III),

Formula (III)

wherein X is 1,2-butanediol, 1,2-pentanediol, 1,2-hexanediol, 1,2-heptanediol (S)-1,2-butanediol, (R)-1,2-butanediol, (S)-1,2-pentanediol, (R)-1,2-pentanediol, (S)-1,2-hexanediol, (R)-1,2-hexanediol, (S)-1,2-heptanediol or (R)-1,2-heptanediol or mixture or hydrates thereof.

In general the compound of Formula (III) may be monohydrate, dihydrates or higher hydrates.

The solvates are compounds formed by solvation, which is the combination of solvent molecules with molecules or ions of the solute. Solvation is an interaction of a solute with the solvent, which leads to stabilization of the solute species in the solution. One may also refer to the solvated state, whereby an ion in a solution is complex by solvent molecules. The difference in the physical properties of different solvates and polymorphic forms thereof results from different orientation and intermolecular interactions of adjacent molecules in the solid. Polymorphic forms of compounds or solvates can be distinguished by x-ray diffraction and by other methods such as, infrared spectroscopy or Raman spectroscopy.

In another general aspect there is provided a process for the preparation of dapagliflozin solvates of Formula (III), Formula (III)

wherein X is 1,2-butanediol, 1,2-pentanediol, 1,2-hexanediol, 1,2-heptanediol, (S)-1,2-butanediol, (R)-1,2-butanediol, (S)-1,2-pentanediol, (R)-1,2-pentanediol, (S)-1,2-hexanediol, (R)-1,2-hexanediol, (S)-1,2-heptanediol or (R)-1,2-heptanediol or mixture or hydrates thereof, the process comprising:

(a) preparing a solution of dapagliflozin in one or more solvents;
(b) adding a diol and one or more second solvents to obtain a reaction mixture;
(c) stirring the reaction mixture at 0-5° C.; and
(d) obtaining the dapagliflozin solvate.

In general, the solvents in the steps (a) and (b) comprises one or more of di-isopropyl ether, methyl-t-butyl ether, diethyl ether, isopropyl acetate, ethyl acetate, hexane, heptane, 1,4-dioxane, tetrahydrofuran, and tetrahydropyran or mixture thereof.

In general, the diol in the step (b) comprises one or more of 1,2-butanediol, 1,2-pentanediol, 1,2-hexanediol, 1,2-heptanediol (S)-1,2-butanediol, (R)-1,2-butanediol, (S)-1,2-pentanediol, (R)-1,2-pentanediol, (S)-1,2-hexanediol, (R)-1,2-hexanediol, (S)-1,2 heptanediol or (R)-1,2-heptanediol.

In another general aspect there is provided a compound of Formula (II),

Formula (II)

In another general aspect the dapagliflozin 1,2-butanediol monohydrate is crystalline.

In another general aspect the crystalline dapagliflozin 1,2-butanediol monohydrate is characterized by a powder X-ray diffraction pattern having characteristic peaks as expressed at about 3.9°, 15.2°, 15.7°, 17.1°, 18.7°, 19.0°, 19.9°, 20.2°, 21.4°, 23.9°, 24.3° and 25.2°±0.2° 2θ.

In general, the crystalline dapagliflozin 1,2-butanediol monohydrate is further characterized by a powder X-ray diffraction pattern having characteristic peaks as expressed at about 7.7°, 8.1°, 8.7°, 11.0°, 13.8°, 22.8°, 24.8°, 26.2°, 26.6°, 27.6°, 28.1°, 30.5° and 38.4°±0.2° 2θ.

In another general aspect the crystalline dapagliflozin 1,2-butanediol monohydrate is characterized by differential scanning calorimetry (DSC) thermogram having endothermic event at about 63.4° C.

Figure 1:
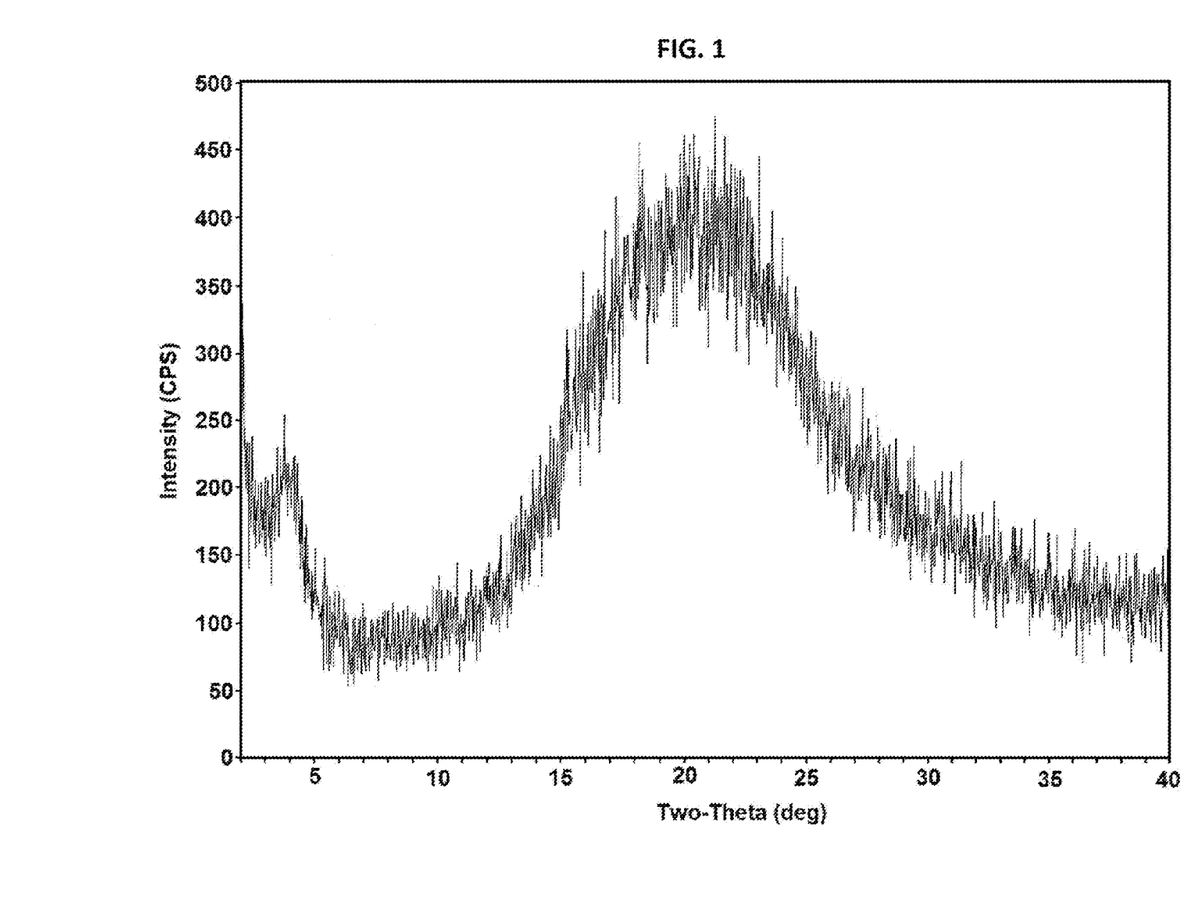
FIG. 1: X-ray diffractogram (XRD) of amorphous dapagliflozin obtained in Example 1.
Figure 2:
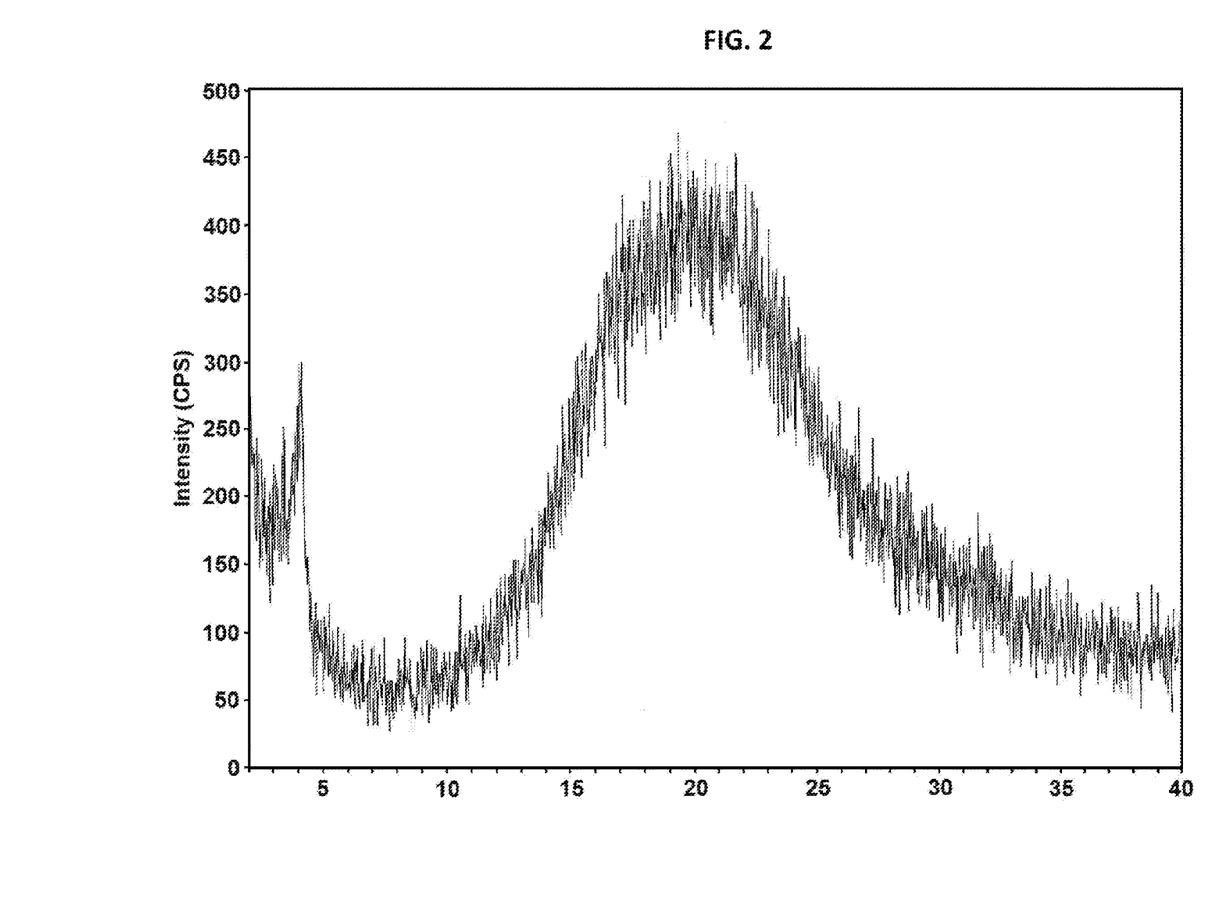
FIG. 2: X-ray diffractogram (XRD) of amorphous dapagliflozin obtained in Example 2.
Figure 3:
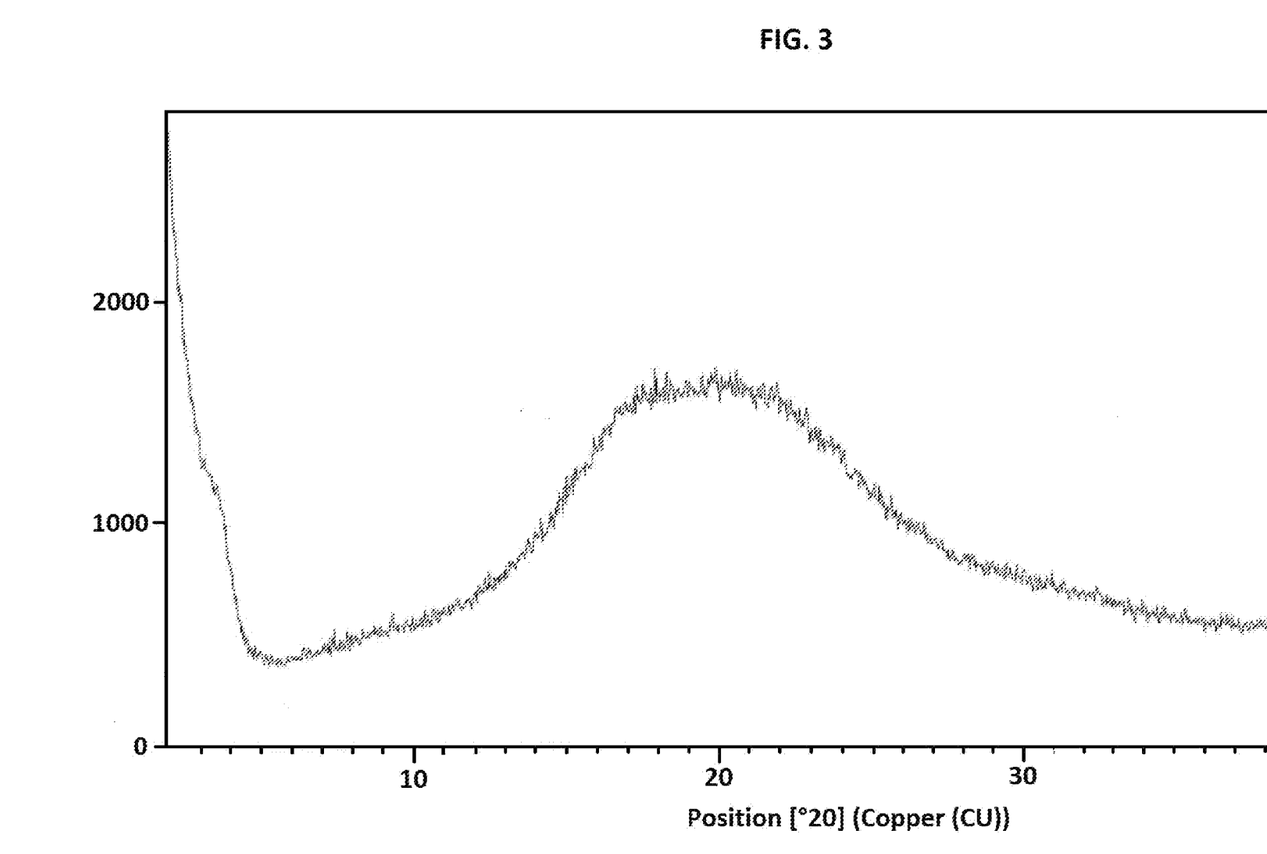
FIG. 3: X-ray diffractogram (XRD) of amorphous dapagliflozin obtained in Example 5.
Figure 4:
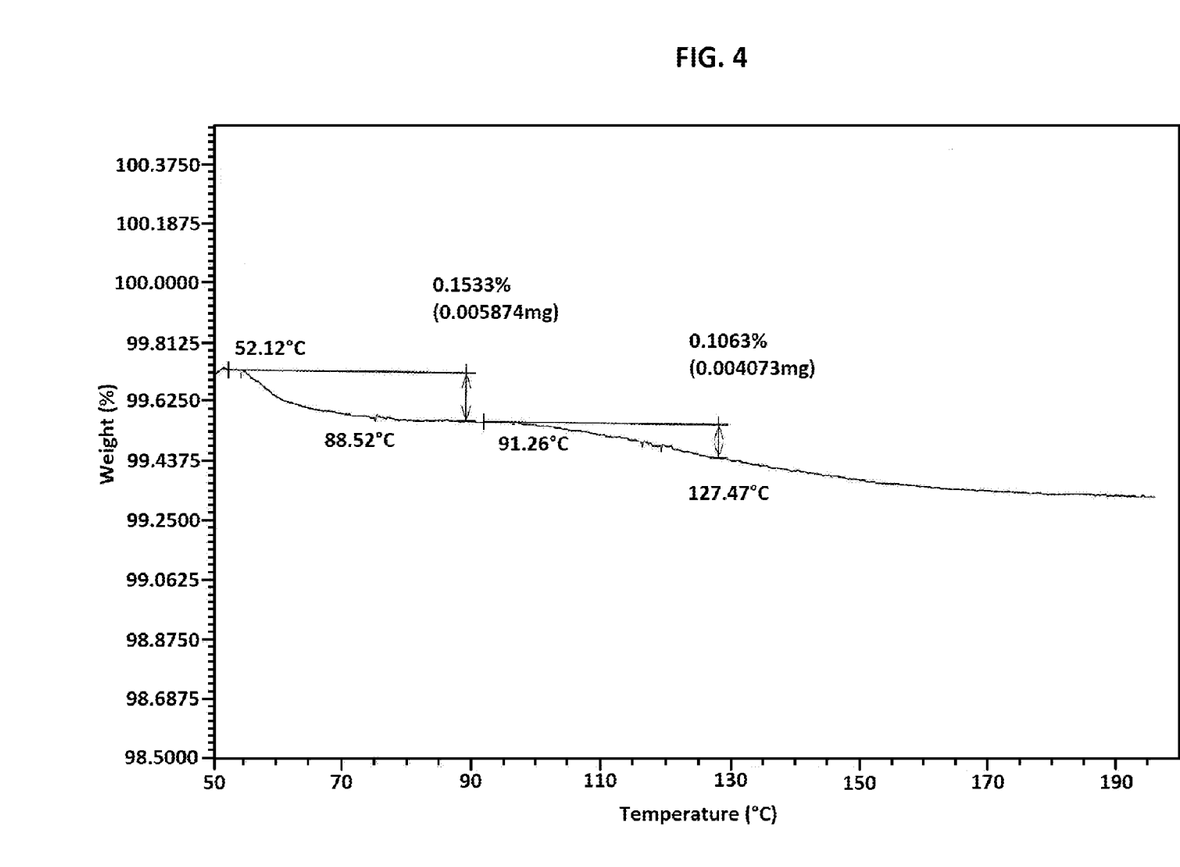
FIG. 4: Thermogravimetric Analysis (TGA) of amorphous dapagliflozin.
Figure 5:
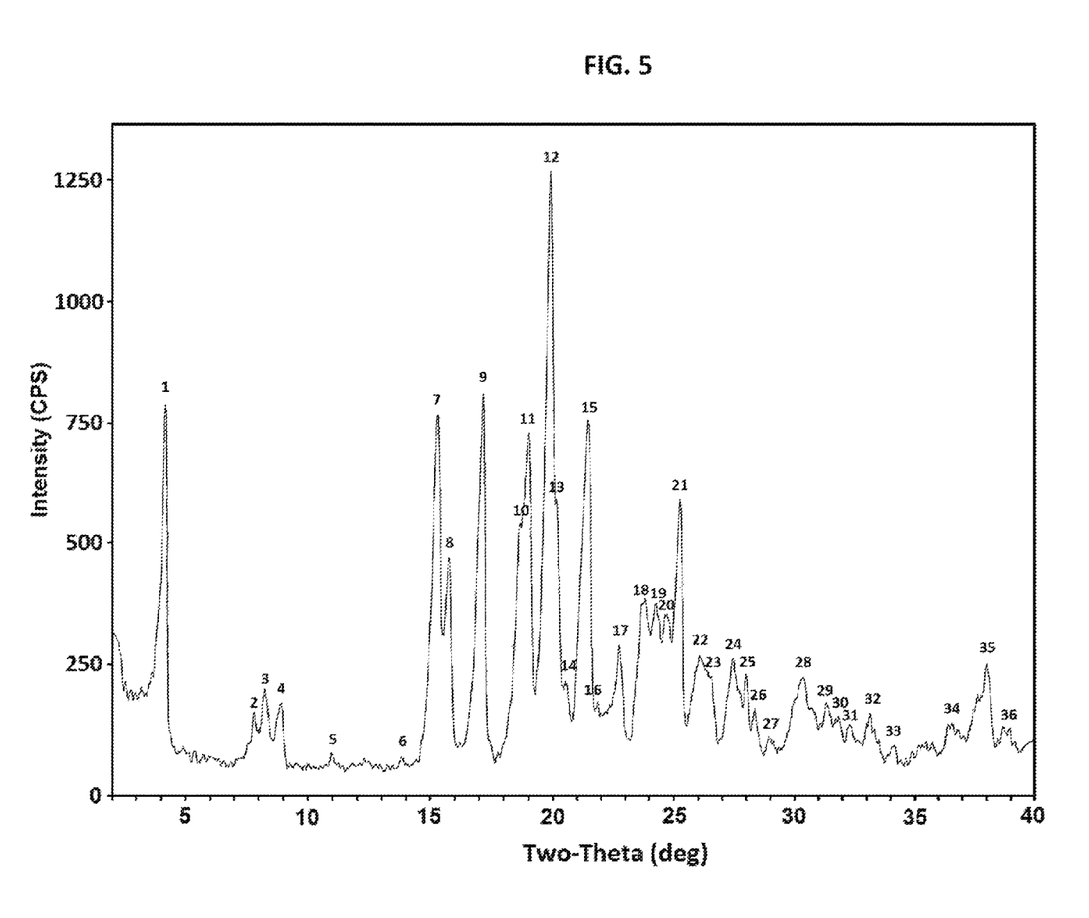
FIG. 5: X-ray diffractogram (XRD) of crystalline 1,2-butanediol solvate of dapagliflozin.
Figure 6:
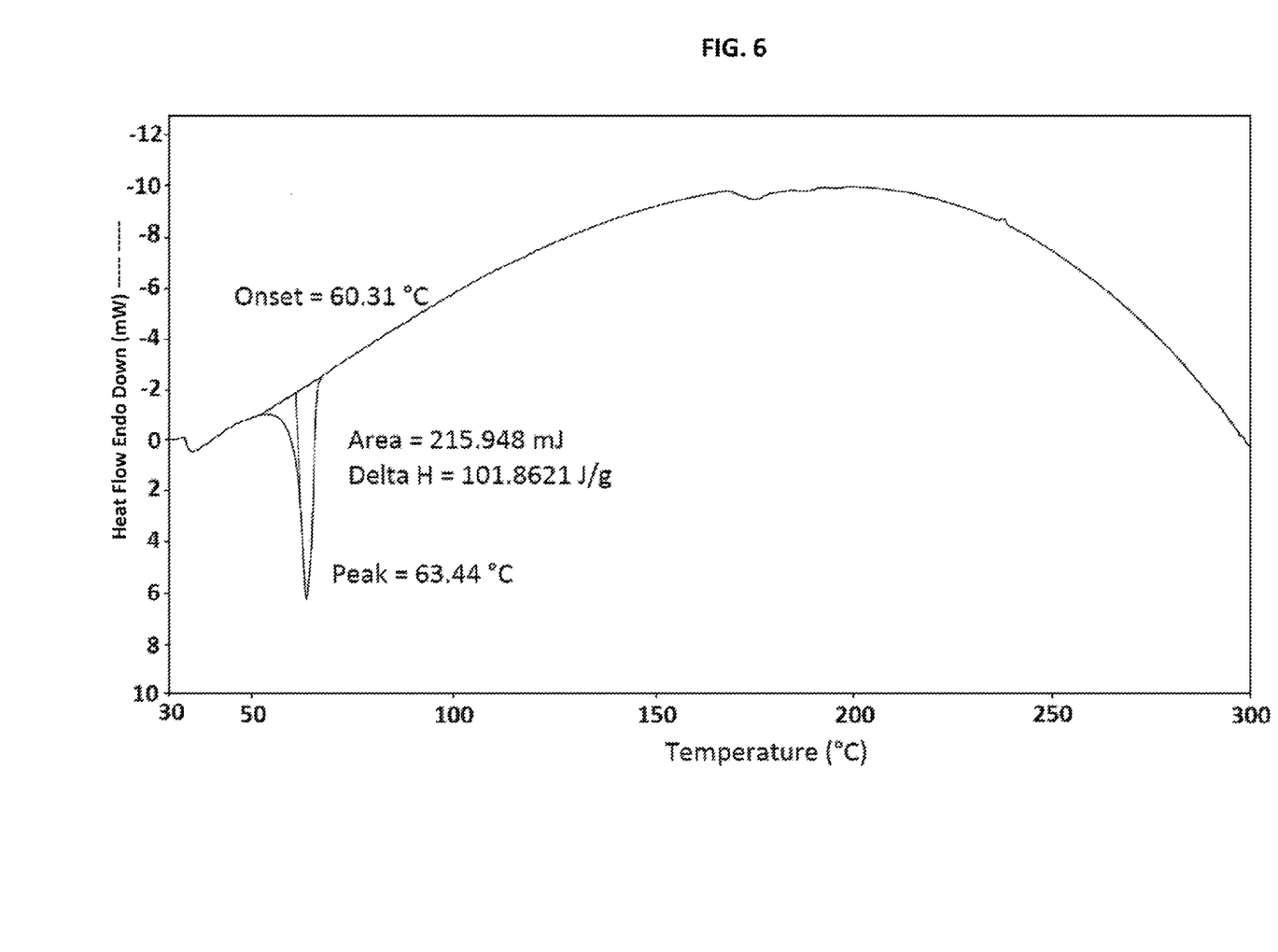
FIG. 6: Differential scanning thermogram (DSC) of crystalline 1,2-butanediol solvate of dapagliflozin.
Figure 7:
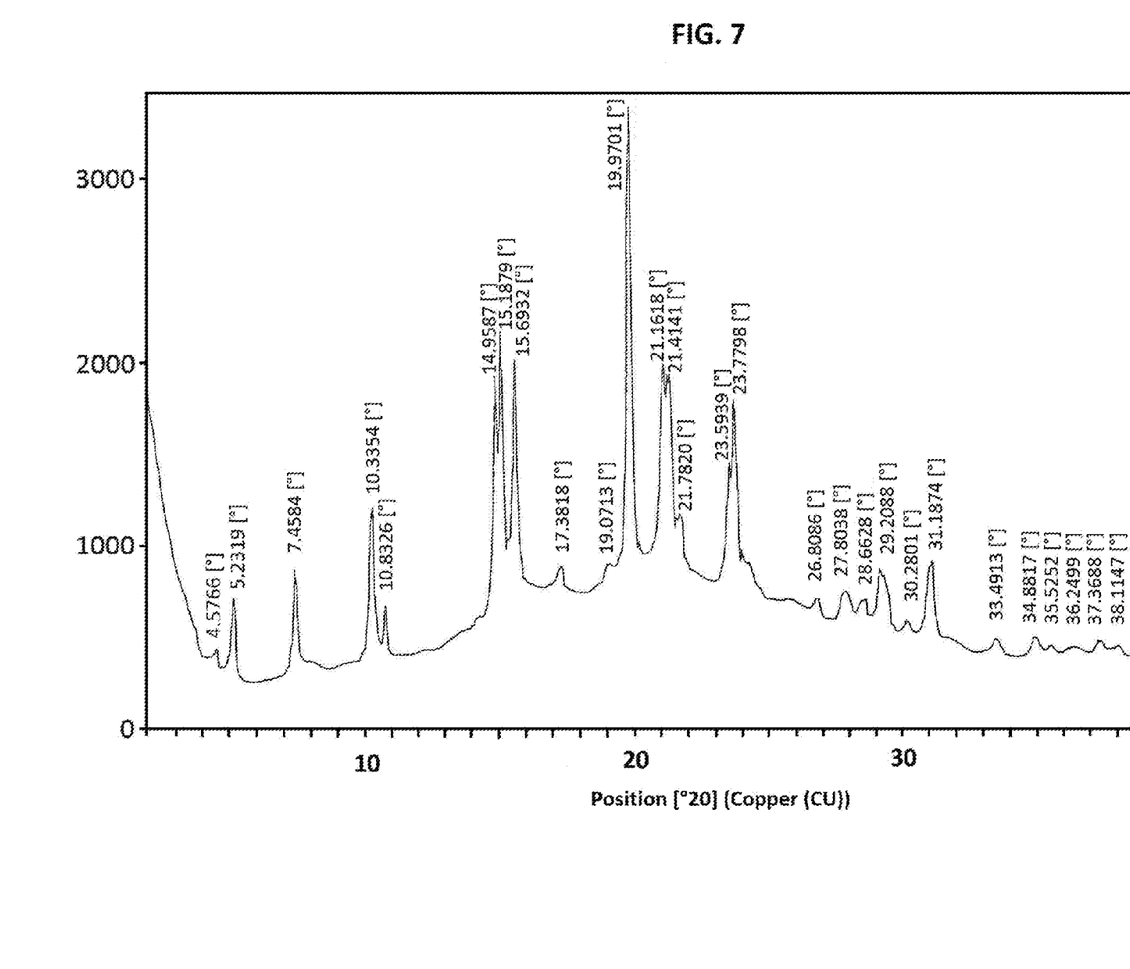
FIG. 7: Illustrates XRPD of crystalline Form Z of dapagliflozin.

In another general aspect the crystalline dapagliflozin 1,2-butanediol monohydrate is characterized by x-ray powder diffraction substantially same as that as depicted in FIG. 1 and differential scanning thermogram (DSC) substantially same as that as depicted in FIG. 2.

In another general aspect the dapagliflozin 1,2-butanediol monohydrate of Formula (II), Formula (II)

the process comprising:
(a) preparing a solution of dapagliflozin in one or more solvents;
(b) adding 1,2-butane diol and one or more second solvents to obtain a reaction mixture;
(c) stirring the reaction mixture at 0-5° C.; and
(d) obtaining the dapagliflozin 1,2-butanediol monohydrate.

In general, the solvents in steps (a) and (b) comprises one or more of di-isopropyl ether, methyl-t-butyl ether, diethyl ether, isopropyl acetate, ethyl acetate, hexane, heptane, 1,4-dioxane, tetrahydrofuran, and tetrahydropyran, or mixture thereof.

In general, the dapagliflozin can be prepared by the processes described in prior art, for an example, as described in U.S. Pat. No. 6,515,117 B2, which is incorporated herein by reference.

In another general aspect, there is provided a stable amorphous dapagliflozin that does not convert to any other solid form when stored at a temperature of up to about 40° C. and at a relative humidity of about 25% to about 75% for about three months or more.

In another general aspect there is provided a process for the preparation of an amorphous dapagliflozin comprising contacting dapagliflozin with water followed by removal of water.

In another general aspect there is provided a process for the preparation of an amorphous dapagliflozin, the process comprising:
(a) contacting dapagliflozin with water to obtain a first reaction mixture,
(b) adding one or more solvents to the first reaction mixture to obtain a second reaction mixture, and
(c) removing the water and the solvent from the second reaction mixture to obtain an amorphous dapagliflozin.

In general, the dapagliflozin required as a starting material for the processes described herein may be obtained by synthetic methods known in the art. The dapagliflozin used herein for contacting with water may be obtained as a result of a synthesis process and/or as an intermediate obtained during its process for preparation or purification.

It is therefore understood that dapagliflozin before being contacted with water may or may not be contacted with water or any other solvent that may be used in the synthesis or purification of dapagliflozin. It is therefore further understood that dapagliflozin contacted with water or one or more solvents before being contacted with water, and optionally with one or more solvents, for performing the processes of the present invention also forms the scope of the specification. The optional contacting with solvents may even be performed prior to contacting with water.

In general the dapagliflozin and the water may be mixed to obtain the reaction mixture or the first reaction mixture. If required, the reaction mixture or the first reaction mixture may further be heated.

In general, the solvents for addition to the first reaction mixture is selected from one or more of the group comprising of alcohols, ketones, esters, amines, aminoalcohols, ethers, amides, nitriles, hydrocarbons and halohydrocarbons; or mixture thereof. In particular, the solvent is selected from alcohols, amines and aminoalcohols.

In general, the alcohols comprises one or more of methanol, ethanol, isopropanol, n-propanol, n-butanol, isobutanol, 2-butanol, benzyl alcohol, ethylenediol, 1,4-butanediol, 1,2-propanediol, 1,3-propanediol, 2-ethoxyethanol, glycerol, propyleneglycol, trimethyleneglycol, and tetrahydrofuran-3-ol; ketones comprises one or more of acetone, methyl ethyl ketone, methyl isobutyl ketone, methyl isopropyl ketone, acetophenone, and cyclopentanone; esters comprises one or more of ethyl acetate, isopropyl acetate and methyl acetate; amines comprises one or more of pyridine, piperidine, ethylenediamine, diethylenetriamine, diethylamine, triethylamine, and morpholine; aminoalcohols comprises one or more of ethanolamine, diethanolamine, triethanolamine, 1-amino-3-propanol, 1-amino-2-propanol, 2-amino-1-propanol, 1-amino-4-butanol, and 3-amino-4-butanol; ethers comprises one or more of diethyl ether, diiopropyl ether, 1,4-dioxane, tetrahydrofuran, and tetrahydropyran; amides comprises one or more of formamide, N,N-dimethyl formamide, N,N-dimethyl acetamide, 2-pyrrolidone, and N-methyl-2-pyrrolidone; nitriles comprises one or more of acetonitrile, and benzonitrile; hydrocarbons comprises one or more of n-hexane, n-heptane, cyclohexane, toluene, and xylene; and halohydrocarbons comprises one or more of methylenedichloride, chloroform, and carbon tetrachloride.

In general, the water from the first reaction mixture or the water and the solvent from the second reaction mixture may be removed by known separation methods to obtain the amorphous dapagliflozin. In general, the water or the mixture of water and solvent may be removed by decantation, filtration, solvent evaporation, solvent evaporation at reduced pressure, spray drying, freeze drying or lyophilization to obtain the amorphous dapagliflozin. In particular, the water or the mixture of water and solvent mixture may be removed by filtration to obtain the amorphous dapagliflozin.

In general, the dapagliflozin and the water are heated and allowed to cool to room temperature; if required, further cooled to 5-10° C. The reaction mixture was than filtered to obtain the amorphous dapagliflozin.

In general, dapagliflozin, water and the solvent are heated and allowed to cool to room temperature; if required, further cooled to 5-10° C. The reaction mixture was than filtered to obtain the amorphous dapagliflozin.

In general, the reaction mixture under heating may be stirred for 30 min to about 5 hours. In particular for about 2 hours to 4 hours. The reaction mixture after being cooled to 5-10° C. was further maintained under stirring for 4 hours to 15 hours. In particular for 12 hours.

In another general aspect there is provided a process for the preparation of stable amorphous dapagliflozin, the process comprising:
(a) treating dapagliflozin or its solvates with water to obtain a reaction mixture;
(b) stirring the reaction mixture at 80° C. to 90° C.;
(c) cooling the reaction mixture at 70° C. to 75° C. and adding isopropyl alcohol,
(d) stirring the reaction mixture at 5° C. to 10° C. for 16-18 hours;
(e) filtering the product,
(f) drying the product under vacuum for 20 to 24 hours below 25° C.;
(g) drying the product under vacuum for 20 to 24 hours at 25° C. to 30° C.;
(h) drying the product under vacuum for 18 to 20 hours at 35° C. to 40° C. till water content is less than 3.0% as measured by KF; and
(i) optionally drying the product under vacuum for 18 to 21 hours at 40° C. to 45° C. to obtain the stable amorphous dapagliflozin.

In general, the dapagliflozin solvates in the step (a) comprises one or more 1,2-butanediol, 1,2-pentanediol, 1,2-hexanediol, 1,2-heptanediol (S)-1,2-butanediol, (R)-1,2-butanediol, (S)-1,2-pentanediol, (R)-1,2-pentanediol, (S)-1,2-hexanediol, (R)-1,2-hexanediol, (S)-1,2-heptanediol or (R)-1,2-heptanediol or mixture or hydrates thereof, which may be monohydrate, dihydrates or higher hydrates.

In another general aspect there is provided a process for preparation of amorphous dapagliflozin, the process comprising:
(a) treating dapagliflozin 1,2-butanediol monohydrate with water to obtain a reaction mixture;
(b) stirring the reaction mixture at 80° C. to 90° C.,
(c) cooling the reaction mixture at 70° C. to 75° C. and adding isopropyl alcohol:
(d) stirring the reaction mixture at 5° C. to 10° C. for 16-18 hours;
(e) filtering the product;
(f) drying the product under vacuum for 20 to 24 hours below 25° C.,
(g) drying the product under vacuum for 20 to 24 hours at 25° C. to 30° C.;
(h) drying the product under vacuum for 18 to 20 hours at 35° C. to 40° C. till water content is less than 3.0% a measured by KF; and
(i) optionally drying the product under vacuum for 18 to 21 hours at 40° C. to 45° C. to obtain the stable amorphous dapagliflozin.

The drying above 30° C. is performed under the controlled humidity conditions. The controlled humidity is in the range of 45 to 55% and at 5-12 mbar vacuums. In particular, the drying at 35° C. to 40° C. and at 40° C. to 45° C. is performed under controlled humidity conditions.

In general, the dapagliflozin 1,2-butanediol monohydrate may be prepared by the process comprising:
(a) preparing a solution of dapagliflozin in one or more solvents;
(b) adding 1,2-butane diol and one or more second solvents to obtain a reaction mixture;
(c) stirring the reaction mixture at 0-5° C.; and
(d) obtaining the dapagliflozin 1,2-butanediol monohydrate.

In general, the dapagliflozin can be prepared by the processes described in prior art, for an example, as described in U.S. Pat. No. 6,515,117 B2, which is incorporated herein by reference.

In general, the solvents in the step (a) and (b) comprises from one or more of di-isopropyl ether, methyl-t-butyl ether, diethyl ether, isopropyl acetate, ethyl acetate, hexane, heptane, 1,4-dioxane, tetrahydrofuran, and tetrahydropyran or mixture thereof.

Thermogravimetric Analysis (TGA) of amorphous dapagliflozin was obtained using TA Instruments (TGA) Thermogravimetric analyzer.

In another general aspect, there is provided a crystalline Form Z of dapagliflozin.

In another general aspect, there is provided a crystalline Form Z of dapagliflozin, characterized by having an x-ray powder diffraction pattern comprising peaks expressed in degrees 2θ (±0.2° 2θ) at about 10.3°, 14.9°, 15.2°, 15.7°, 20.0°, 21.2° and 23.8°±0.2°2θ.

The crystalline Form Z of dapagliflozin, can be further characterized by having an X-ray powder diffraction pattern comprising peaks expressed in degrees 2θ±0.2° at about 4.6°, 5.2°, 7.4°, 10.8°, 17.4°, 21.4°, 21.8°, 23.6°, 26.8°, 27.8°, 28.7°, 29.2°, 30.3°, 31.2° and 33.5°±0.2° 2θ.

In another general aspect, the crystalline Form Z of dapagliflozin is characterized by having X-ray powder diffraction pattern substantially the same as that shown in FIG. 1.

In another general aspect, there is provided a process for the preparation of crystalline Form Z of dapagliflozin, the process comprising:
(a) preparing a suspension of dapagliflozin 1,2-butanediol in water;
(b) heating the suspension at 75° C. to 90° C. to obtain a solution;
(c) adding one or more solvents to the solution to obtain a reaction mixture;
(d) cooling the reaction mixture; and
(e) obtaining the crystalline Form Z of dapagliflozin.

In general, the dapagliflozin 1,2-butane diol used for the preparation of crystalline Form Z can be prepared by reacting dapagliflozin with 1,2-butanediol.

In general, the dapagliflozin 1,2-butanoldiol used for the preparation of crystalline Form Z is dapagliflozin 1,2-butanoldiol monohydrate.

In general, the suspension of dapagliflozin 1,2-butanediol in water is prepared at about 15° C. to about 35° C.

The suspension in step (a) is heated from about 50° C. to about 120° C. In particular, the suspension is heated from about 75° C. to about 90° C. to obtain a solution.

In general, the solvent in step (c) comprises one or more of $C_1$-C alcohols, 1,2-propanediol and 1,2-butanediol. In particular, isopropanol may be used.

The reaction mixture obtained in step (c) may be cooled to about 30° C. or less. In particular, the reaction mixture may be cooled to 15° C. or less.

In another general aspect there is provided a stable amorphous form and crystalline solvates of dapagliflozin which is stable during storage and drying.

Powder X-ray Diffraction of amorphous dapagliflozin and crystalline Form Z of dapagliflozin was obtained under following conditions:
Instrument: X-Ray Diffractometer, P/W3050/60, Make: PANalytical
Generator Setting:
Tension: 45 KV
Current: 40 mA Scan axis: Gonio
Divergence slit: Automatic
Goniometer radious: 240.0
Distance focus divergence slit: 100.0 mm
Incident Beam Side:
Offset: 0.000
Sollar slit: 0.02° rad
Beam mask: 10 mm
Divergance slit: PDS (Automatic)
Anti scatter slit: ½°
Filter: None
Beam attenuator: None
Diffracted Beam Side:
Offset: 0.000
Sollar slit: 0.02° rad
Receiving slit: None
Anti scatter slit: 8 mm (PIXcel)
Filter: Large beta filter Nickel
Beam attenuator: None
Detector: PIXcel 1D-Medipix3
Mode: Scanning line detector (1D)
Active length: 3.347° 2θ
Number of active channels: 255

Method Parameter:
Start position (° 2θ): 2
End position (° 2θ): 40
Step size (s): 0.02
Time per step: 67.575
Scan mode: Continuous
Spinning: 1 revolution/sec Powder X-ray Diffraction of crystalline solvate of dapagliflozin can be obtained under following conditions.
Instalment: X-Ray DifFractometer, D/Max-2200/PC, Make: Rigaku, or PANalytic-al Expertpro or equivalent.
X-Ray: Cu/40 kv/40 mA
Diverging Slit: 1°
Scattering Slit: 1°
Receiving Slit: 0.15 mm
Monochromator RS: 0.8 mm
Counter: Scintillation Counter
Scan Mode: Continuous
Scan Speed: 3.000°/min
Sampling Width: 0.020°
Scan Axes: Two Theta vs cps
Scan Range: 2° to 40.0°
Theta Offset: 0.000°

Differential scanning calorimetric analysis was performed using a Perkin Elmer Diamond DSC control unit and a differential scanning calorimeter. 2-5 mg samples were placed in crimped aluminum pans and heated from 30° C. to 300° C. in a liquid nitrogen atmosphere at a heating rate of 10° C./minute.

In another general aspect there is provided a pharmaceutical composition comprising a therapeutically effective amount of crystalline 1,2-butanediol dapagliflozin solvate and one or more pharmaceutically acceptable carriers, excipients or diluents.

In another general aspect the stable amorphous form and crystalline forms of dapagliflozin are stored under nitrogen atmosphere and packed in a double polythene bag tied with a thread, keeping primary packing containing the stable amorphous form or crystalline forms of dapagliflozin inside a black color polyethylene bag containing oxygen busters and sealing it, placing above the double polyethylene bag inside a triple laminated bag optionally containing oxygen busters and sealing it, and placing the sealed triple laminated bag inside a closed high density polyethylene (HDPE) container and storing in controlled environment chamber at about 25° C. to 40° C.

In general, the stable crystalline Form Z of dapagliflozin doesn't convert to known crystalline forms or amorphous form of dapagliflozin upon storage in controlled environment chamber at about 25° C.

In another general aspect the storage stable amorphous dapagliflozin may be characterized by at least three months stability results as outline in Table-I which is representative for one of the batch.

TABLE I

| Sr. No. | Tests | Specifications | Initial | 1 Month 40° C. ± 2° C./75% ± 5% RH | 2 Months 40° C. ± 2° C./75% ± 5% RH | 3 Months 40° C. ± 2° C./75% ± 5% RH |
|---|---|---|---|---|---|---|
| 1. | Description | White to slightly yellow powder | White Powder | White Powder | White Powder | White Powder |
| 2. | Polymorph | Amorphous | Amorphous | Amorphous | Amorphous | Amorphous |

In another general aspect there is provided an amorphous dapagliflozin having purity of about 99% or more by area percentage of HPLC. In particular, the purity of about 99.5% or more, more particularly, the purity of about 99.8% or more, further more particularly, the purity by HPLC of about 99.9% s or more, when measured by area percentage of HPLC.

In general, the amorphous dapagliflozin has particle size distribution as characterized by 90% particles having particle size (D90) less than 250 µm, 50% particles having particle size (D50) less than 100 urn and 10% particles having particle size (D10) less than 50 µm.

In general, the amorphous dapagliflozin may be micronized to achieve the better particle size distribution in order to make suitable Formulation.

In another general aspect there is provided a pharmaceutical composition comprising a therapeutically effective amount of stable amorphous dapagliflozin and one or more pharmaceutically acceptable carriers, excipients or diluents.

The present invention is further illustrated by the following examples which are provided merely to exemplify the invention and do not limit the scope of the invention. Any obvious modification(s) of the process(es) of the present invention and routine experimentation are also within the scope of this specification; such modification(s) and/or experimentation are, for example but not limited to, heating or cooling any of the solution, slurry or mixture; altering the rate of heating or cooling of the same; altering the quantity of water and/or the organic solvent; using different rate of adding or mixing the components of the solution or reaction mixture; using solvent combinations from same or the different groups of solvents described herein; are to name a few.

EXAMPLES

Example-1: Preparation of Amorphous Dapagliflozin

In a 250 mL four necked round bottom flask equipped with nitrogen atmosphere facility, mechanical stirrer, thermometer and an addition funnel, dapagliflozin (5 g) and water (60 mL) were heated to 80-90° C., stirred for 2 hours and allowed to cool to 25-35° C. The reaction mixture was further cooled to 5-10° C. and stirred for 12 hours. The resulting mass was filtered, washed with water and dried to obtain amorphous dapagliflozin having 99.8% HPLC purity.

Example-2: Preparation of Amorphous Dapagliflozin

In a 250 mL four necked round bottom flask equipped with nitrogen atmosphere facility, mechanical stirrer, thermometer and an addition funnel, dapagliflozin (5 g), water (60 mL) and isopropanol (1.5 mL) were heated to 80-90° C., stirred for 2 hours and allowed to cool to 25-35° C. The reaction mixture was further cooled to 5-10° C. and stirred for 12 hours. The resulting mass was filtered, washed with water and dried to obtain amorphous dapagliflozin having 99.85% HPLC purity and residual solvent less than 0.1% by GC.

Example-3: Preparation of Amorphous Dapagliflozin

In a 250 mL four necked round bottom flask equipped with nitrogen atmosphere facility, mechanical stirrer, thermometer and an addition funnel, dapagliflozin (5 g) and water (60 mL) were heated to 80-90° C., 1-amino-2-propanol (1.5 mL) was added and stirred for 1.5 hours and cooled to 25-35° C. The reaction mixture was further cooled to 5-10° C. and stirred for 12 hours. The resulting mixture was filtered, washed with water and dried to obtain amorphous dapagliflozin having 99.8% HPLC purity and residual solvent less than 0.1% by GC.

Example-4: Preparation of dapagliflozin 1,2-butanediol monohydrate

In a round bottom flask, 53 g dapagliflozin and 159 mL methyl tertiary butyl ether were taken and stirred for 15 minutes at 25-35° C. The reaction mixture was stirred at 40° C. to 45° C. for 15 minutes and then filtered and washed with 53 mL methyl tertiary butyl ether. The filtrate was taken in another flask and 23.4 g of 1,2-butanediol and 4.7 g water were added and the reaction mixture was stirred at 25° C. to 35° C. for 10-15 minutes. The reaction mixture was warmed to 40° C. to 45° C. and 318 mL diisopropyl ether was added. The reaction mixture was stirred at 40° C. to 45° C. for 10-15 minutes. The reaction mixture was cooled to 25° C. to 35° C. and then cooled to 0° C. to 5° C. and stirred at this temperature for 3-4 hours. The product thus obtained (or obtained by seeding of dapagliflozin 1,2-butanediol) was filtered and washed with pre-cooled diisopropyl ether. The wet product and 106 mL methyl tertiary butyl ether were taken in another flask and stirred at 25° C. to 35° C. for 10-15 minutes. The reaction mixture then stirred at 35° C. to 40° C. for 10-15 minutes. 212 mL diisopropyl ether was added slowly into the reaction mixture and stirred at 35° C. to 40° C. for 25-30 minutes. The reaction mixture was cooled to 25° C. to 35° C. and then stirred at 0° C. to 5° C. for an hour. The product was filtered and washed with pre-cooled diisopropyl ether. The wet product was taken in another flask. 212 mL toluene was added and the reaction mixture was stirred at 40° C. to 50° C. to get clear solution. 424 mL diisopropyl ether was added slowly into the reaction mixture and stirred for 15-20 minutes. The reaction mixture then cooled to 25° C. to 35° C. and then stirred at 0° C. to 5° C. for an hour. The solid was filtered and washed with pre-cooled diisopropyl ether. The product was dried at 25° C. to 35° C. for an hour and then further dried under vacuum at 40° C. to 45° C. for 8-12 hours to obtain dapagliflozin 1,2-butane diol monohydrate.

Example-5: Preparation of Amorphous Dapagliflozin 30 g of dapagliflozin-1,2-butanediol monohydrate and 450 ml water were taken in a round bottom flask and stirred for 15 minutes at 25° C. to 35° C. and then stirred at 80° C. to 90° C. for an hour. The reaction mixture then slowly cooled to 70° C. to 75° C. and 7.0 gm isopropyl alcohol was added at 70° C. to 75° C. The reaction mixture then cooled to 25° C. to 35° C. The reaction mixture was stirred at 5° C. to 10° C. for 16-18 hours. The reaction product was filtered and washed with pre-cooled water.

The product was dried under vacuum for 24 hours below 25° C. The product was further dried under vacuum for 20 to 24 hours at 25° C. to 30° C. The product then dried under vacuum at 35° C. to 40° C. for 18-20 hours till water content less than 3.0% (humidity 45-55% & 5-12 mbar vacuum). The product was processed in a mixer to obtain a grounded mixture at below 25° C. (humidity 45-55% & 5-12 mbar vacuum). The product was then dried under vacuum at 35° C. to 40° C. for 17 hours. The product was further dried under vacuum at 40° C. to 45° C. for 18-21 hours to obtain amorphous dapagliflozin (water content not more than 3.0% as measured by KF).

Example-6: Preparation of dapagliflozin 1,2-butane diol solvate

In a round bottom flask, 1 g dapagliflozin was dissolved in 5 mL diisopropyl ether and 0.44 g of 1,2-butanediol was added. The reaction mixture was stirred of 30 min at 30° C. 10 mL methyl-butyl ether was added slowly into the reaction mixture and stirred at 0-5° C. for 1 hour. The product was filtered and washed with a mixture of diisopropyl ether and methyl-tert-butyl ether and dried at 35° C. for 12 hours to obtain dapagliflozin 1,2-butanediol solvate.

Example-7: Preparation of dapagliflozin 1,2-butane diol solvate

In a round bottom flask, 3 g dapagliflozin was dissolved in 27 mL methyl-tert-butyl ether and 1.32 g of 1,2-butane diol was added. The reaction mixture was stirred for 30 min at 30° C. 27 mL di-isopropyl ether was added slowly into the reaction mixture and stirred at 0-5° C. for 1-2 hours. The product was filtered and washed with diisopropyl ether and dried at 35° C. for 12 hours to obtain dapagliflozin 1,2-butane diol solvate.

Example-8: Preparation of dapagliflozin 1,2-butanediol solvate

In a round bottom flask, 0.5 g dapagliflozin was taken in 25 mL diisopropyl ether and 0.21 g of 1,2-butanediol and 0.043 g of water were added. The reaction mixture was stirred at 55° C. for 1-2 hours then cooled to 25 to 35° C. The reaction mixture was then cooled to 0 to 5° C. and 2.5 mL hexane was added slowly at 0 to 5° C. and stirred for 12 hours at 0 to 5° C. The product was filtered and washed with hexane and then dried at 35° C. for 12 hours to obtain dapagliflozin 1,2-butanediol solvate.

Example-9: Preparation of Form Z of Dapagliflozin

In a round bottom flask, 5.0 g dapagliflozin 1,2-butane diol was added in 75 mL of water. The reaction mixture was heated to 80° C. to 90° C. and stirred for 1 hour. The clear solution was cooled to 70° C. and 1.2 g isopropanol was added. The reaction mixture was stirred for 30 min and cooled to 30° C. and stirred for 1 hour. The reaction mixture was further cooled to 5° C. to 10° C. and stirred for 16 hours. The product was filtered and washed with water and dried at below 25° C. under vacuum for 12-14 hours to obtain crystalline Form Z of dapagliflozin.

Example-10: Preparation of Form Z of Dapagliflozin

In a round bottom flask, 5.0 g dapagliflozin 1,2-butane diol was added in 75 mL water. The reaction mixture was heated to 80° to 90° C. and stirred for 1 hour. The clear solution was cooled to 70° C. and 1 g isopropanol was added. The reaction mixture was stirred at 65-70° C. and then slowly cooled to 25-30° C. and stirred 30 min and cooled to 5° to 10° C. and stirred for 12 to 16 hours. The product was filtered and washed with water and dried at below 25° C. under vacuum for 24 hours to obtain crystalline Form Z of dapagliflozin.

Example-11: Preparation of Amorphous Dapagliflozin

148 g of dapagliflozin 1,2-butanediol monohydrate, 740 mL ethyl acetate and 296 mL water were taken in a round bottom flask and stirred for 30 minutes at 25° C. to 35° C. The reaction mixture was allowed to settle and the organic layer and aqueous layer were separated. Aqueous layer was washed with 148 mL ethyl acetate. The organic layers were combined and 296 mL water was added into that. The mixture was stirred for 30 minutes and was allowed to settle and the organic layer and aqueous layer were separated 25° C. to 35° C. Again 296 mL water was added into the ethyl acetate layer and stirred for 30 minutes and was allowed to settle and the organic layer and aqueous layer were separated. The ethyl acetate layer was filtered through hyflo bed with fine filter pad and then filtered using 0.45 micron filter paper. The solvent was distilled under vacuum below 50° C. 2220 mL water was added into the residue at below 50° C. and stirred at 80 to 90° C. for an hour. The reaction mixture was cooled to 70 to 75° C. and 34.5 ml, isopropyl alcohol was added into that. The reaction mixture was cooled slowly to 30-35° C. in 2-3 hours and then cooled to 15 to 20° C. The reaction mixture was seeded with 0.74 g dapagliflozin and stirred for 18 hours at 15 to 20° C. The reaction mixture was then cooled to 5 to 10° C. and stirred at this temperature for 12 hours. The reaction product was filtered and washed with pre-cooled water.

The product was dried under vacuum for 24 hours at 18 to 22° C. The product was further dried under vacuum for 22-24 hours at 18° C. to 22° C. till the water content limit not more than 5.0%. The product was then dried under vacuum at 24° C. to 28° C. for 12 hours at 5 to 10 m bar vacuum. Then the product was dried under vacuum for 6 hours at humidity <55% and 5-10 mbar vacuum. The product was mixed and further dried under vacuum for 18 hours at humidity <55% and 5-10 mbar vacuum. The material was processed in a mixer or a multi mill (by 5 mm followed by 3 mm or 2 mm) at below 25° C. (humidity<55%). The product was dried under vacuum for 12-14 hours at 35 to 40° C. until the moisture content not more than 3.0% (as measured by KF) was obtained and then processed in a multi mill (1 mm mesh) at humidity<55% and 5-10 mbar vacuum. The product was passed through a sieve below 25° C. and humidity<55% (moisture content not more than 3.0%) to obtain amorphous dapagliflozin. Yield: 82.3 to 94.9%.

While the present invention has been described in terms of its specific embodiments, certain modifications and equivalents will be apparent to those skilled in the art and are intended to be included within the scope of the present invention.

We claim:

1. A Dapagliflozin solvate of general Formula (III),

Formula (III)

wherein X is 1,2-butanediol, 1,2-pentanediol, 1,2-hexanediol, 1,2-heptanediol, (S)-1,2-butanediol, (R)-1,2-butanediol, (S)-1,2-pentanediol, (R)-1,2-pentanediol, (S)-1,2-hexanediol, (R)-1,2-hexanediol, (S)-1,2-heptanediol or (R)-1,2-heptanediol, or a hydrate, or a mixture or a hydrate thereof.

2. A process for the preparation of the dapagliflozin solvate of Formula (III) according to claim 1, Formula (III)

wherein X is 1,2-butanediol, 1,2-pentanediol, 1,2-hexanediol, 1,2-heptanediol, (S)-1,2-butanediol, (R)-1,2-butanediol, (S)-1,2-pentanediol, (R)-1,2-pentanediol, (S)-1,2- hexanediol, (R)-1,2-hexanediol, (S)-1,2-heptanediol or (R)-1,2-heptanediol or a mixture or hydrates thereof, the process comprising:
(a) preparing a solution of dapagliflozin in one or more solvents;
(b) adding a diol and one or more second solvents to obtain a reaction mixture;
(c) stirring the reaction mixture at 0-5° C.; and
(d) obtaining the dapagliflozin solvate.

3. The process according to claim 2, wherein the solvents in the steps (a) and (b) comprises one or more of di-isopropyl ether, methyl-t-butyl ether, diethyl ether, isopropyl acetate, ethyl acetate, hexane, heptane, 1,4-dioxane, tetrahydrofuran, and tetrahydropyran, or a mixture thereof.

4. The process according to claim 2, wherein the diol in the step (b) a comprises one or more of 1,2-butanediol, 1,2-pentanediol, 1,2-hexanediol, 1,2-heptanediol, (S)-1,2-butanediol, (R)-1,2-butanediol, (S)-1,2-pentanediol, (R)-1,2-pentanediol, (S)-1,2-hexanediol, (R)-1,2-hexanediol, (S)-1,2-heptanediol or (R)-1,2-heptanediol.

5. A dapagliflozin 1,2-butanediol monohydrate of Formula (II),

Formula (II)

6. The compound according to claim 5 is crystalline dapagliflozin 1,2-butanediol monohydrate characterized by a powder X-ray diffraction pattern having characteristic peaks as expressed at about 3.9°, 15.2°, 15.7°, 17.1°, 18.7°, 19.0°, 19.9°, 20.2°, 21.4°, 23.9°, 24.3° and 25.2°±0.2° 2θ.

7. The crystalline dapagliflozin 1,2-butanediol monohydrate according to claim 6, characterized by differential scanning calorimetry (DSC) thermogram having endothermic event at about 63.4° C.

8. A process for the preparation of the compound dapagliflozin 1,2-butanediol monohydrate of Formula (II) according to claim 5, Formula (II)

the process comprising:
(a) preparing a solution of dapagliflozin in one or more solvents;
(b) adding 1,2-butane diol and one or more second solvents to obtain a reaction mixture;
(c) stirring the reaction mixture at 0-5° C.; and (d) obtaining the dapagliflozin 1,2-butanediol monohydrate.

9. The process according to claim 8, wherein the solvents in the steps (a) and (b) comprises one or more of di-isopropyl ether, methyl-t-butyl ether, diethyl ether, isopropyl acetate, ethyl acetate, hexane, heptane, 1,4-dioxane, tetrahydrofuran, and tetrahydropyran, or mixture thereof.

10. A stable amorphous dapagliflozin that does not convert to any other solid form when stored at a temperature of up to about 40° C. and at a relative humidity of about 25% to about 75% for about three months or more.

11. A process for the preparation of the stable amorphous dapagliflozin according to claim 10, the process comprising:
(a) treating dapagliflozin or its solvates with water to obtain a reaction mixture;
(b) stirring the reaction mixture at 80° C. to 90° C.;
(c) cooling the reaction mixture at 70° C. to 75° C. and adding isopropyl alcohol;
(d) stirring the reaction mixture at 5° C. to 10° C. for 16-18 hours;
(e) filtering the product;
(f) drying the product under vacuum for 20 to 24 hours below 25° C.;
(g) drying the product under vacuum for 20 to 24 hours at 25° C. to 30° C.;
(h) drying the product under vacuum for 18 to 20 hours at 35° C. to 40° C. till water content is less than 3.0% as measured by KF; and
(i) optionally drying the product under vacuum for 18 to 21 hours at 40° C. to 45° C. to obtain the stable amorphous dapagliflozin.

12. The process according to claim 11, wherein the solvates in steps (a) is selected from 1,2-butanediol, 1,2-pentanediol, 1,2-hexanediol, 1,2-heptanediol, (S)-1,2-butanediol, (R)-1,2-butanediol, (S)-1,2-pentanediol, (R)-1,2-pentanediol, (S)-1,2-hexanediol, (R)-1,2-hexanediol, (S)-1,2-heptane diol, (R)-1,2-heptanediol or a mixture or a hydrate thereof.

13. The process for the preparation of the stable amorphous dapagliflozin according to claim 11, the process comprising:
(a) treating dapagliflozin 1,2-butanediol monohydrate with water to obtain a reaction mixture;
(b) stirring the reaction mixture at 80° C. to 90° C.;
(c) cooling the reaction mixture at 70° C. to 75° C. and adding isopropyl alcohol;
(d) stirring the reaction mixture at 5° C. to 10° C. for 16-18 hours;
(e) filtering the product;
(f) drying the product under vacuum for 20 to 24 hours below 25° C.;
(g) drying the product under vacuum for 20 to 24 hours at 25° C. to 30° C.;
(h) drying the product under vacuum for 18 to 20 hours at 35° C. to 40° C. till water content is less than 3.0% as measured by KF; and
(i) optionally drying the product under vacuum for 18 to 21 hours at 40° C. to 45° C. to obtain the stable amorphous dapagliflozin.

14. A pharmaceutical composition comprising a therapeutically effective amount of stable amorphous dapagliflozin according to claim 10 and one or more pharmaceutically acceptable carriers, excipients or diluents for the treatment of diabetes.

15. A method for treating diabetes comprising administering a pharmaceutical composition comprising a therapeutically effective amount of stable amorphous dapagliflozin according to claim 10 and one or more pharmaceutically acceptable carriers, excipients or diluents to a subject in need thereof.

\* \* \* \* \*